(12) United States Patent
Lennemann

(10) Patent No.: US 10,449,214 B2
(45) Date of Patent: Oct. 22, 2019

(54) USE OF HYALURONIC ACID

(71) Applicant: Tracey Lennemann, London (GB)

(72) Inventor: Tracey Lennemann, London (GB)

( * ) Notice: Subject to any disclaimer, the term of this patent is extended or adjusted under 35 U.S.C. 154(b) by 0 days.

(21) Appl. No.: 15/745,744

(22) PCT Filed: Jul. 18, 2016

(86) PCT No.: PCT/EP2016/001253
§ 371 (c)(1),
(2) Date: Jan. 18, 2018

(87) PCT Pub. No.: WO2017/012711
PCT Pub. Date: Jan. 26, 2017

(65) Prior Publication Data
US 2018/0207199 A1   Jul. 26, 2018

(30) Foreign Application Priority Data
Jul. 19, 2015 (DE) .................. 10 2015 009 271

(51) Int. Cl.
| A61K 31/728 | (2006.01) |
| A61P 1/02 | (2006.01) |
| A61C 19/06 | (2006.01) |
| A61F 2/28 | (2006.01) |
| A61K 9/00 | (2006.01) |
| A61K 47/02 | (2006.01) |

(52) U.S. Cl.
CPC .......... *A61K 31/728* (2013.01); *A61C 19/063* (2013.01); *A61F 2/28* (2013.01); *A61K 9/0019* (2013.01); *A61K 47/02* (2013.01); *A61P 1/02* (2018.01); *A61F 2002/2817* (2013.01)

(58) Field of Classification Search
None
See application file for complete search history.

(56) References Cited

U.S. PATENT DOCUMENTS

2007/0196426 A1 * 8/2007 Hermitte ................ A61L 27/26
424/426
2014/0147479 A1   5/2014 Agerup
2014/0274941 A1   9/2014 Anastassiades

FOREIGN PATENT DOCUMENTS

EP   2647649 A1   10/2013
WO   9732591 A1   9/1997

OTHER PUBLICATIONS

Wollina, J Clin Aesthet Dermatol. 2014; 7(10):38-43. (Year: 2014).*
Belotero product catalog, Merz Pharmaceuticals GmBH, May 2014. (Year: 2014).*
Gold, Clinical Interventions in Aging 2007:2(3) 369-376. (Year: 2007).*
Alleman, Clinical Interventions in Aging 2008:3(4) 629-634. (Year: 2008).*
AVSVideos2, Internet video published Aug. 9, 2013, https://www.youtube.com/watch?v=UuM5HsVyWGQ, transcript attached. (Year: 2013).*
Muhn C et al: "The evolving role of hyaluronic acid fillers for facial volume restoration and contouring: A canadian overview" Clinical. Cosmetic and Investigational Dermatology Sep. 27, 2012 Dove Medical Press LTD. NZL. vol. 5. Sep. 27, 2012 (Sep. 27, 2012).

* cited by examiner

*Primary Examiner* — Layla D Berry
(74) *Attorney, Agent, or Firm* — Abel Schillinger, LLP

(57) ABSTRACT

A gel containing hyaluronic acid in a crosslinked form or in a mixture of a crosslinked and non-crosslinked form is injected into the periosteum of a bone in order to heal and/or regenerate bones or tissue surrounding bones in humans or vertebrates.

20 Claims, 2 Drawing Sheets

USE OF HYALURONIC ACID

The present invention refers to a novel use of a gel containing hyaluronic acid in a cross-linked form or as a mixture of cross-linked and non-cross-linked forms.

Hyaluronic acid or hyaluronan (HA) is a glucosaminoglycane and a natural constituent of human and animal bodies, which is predominantly found in connective tissues, including the extracellular matrix (ECM) of peripheral tissues and in the central nervous system (CNS), in the nucleus pulposus of intervertebral discs, in the vitreous body of the human eye, and in the synovia (joint fluid). HA is a polymer consisting of monomeric structural units of the disaccharide of D-glucuronic acid and N-acetyl-D-glucosamine, which are synthesized by HA synthases in the bodies of vertebrates. The polymer chain length is typically 250 to 50,000 disaccharide units, which corresponds to a molecular weight of about 95 kD to about 19,000 kD.

HA has an exceptionally high water binding capacity (up to 6 l water per 1 g HA) and viscoelasticity, which properties are the reason for its value as a structural component.

Due to its complex interactions with matrix components and cells as a result of its physicochemical and biological properties, HA also plays very diverse roles in physiological processes, which are not fully understood by now.

Some important properties of HA, in addition to its structural properties, include a capacity to activate fibroblasts in the skin, a significant bacteriostatic effect of medium- and high-molecular weight HA, an angiogenetic effect of low-molecular weight HA, and, surprisingly, an anti-angiogenetic effect of high-molecular weight HA as well as an osteogenic effect.

In human medicine including aesthetic medicine, non-animal, biotechnologically derived recombinant HA is presently used in non-crosslinked or partially cross-linked forms mainly for injections into the joint space of arthritic joints, in dentistry for injection into periodontal ligaments, in hydrogels for wound care, in nasal sprays and eye drops, for wrinkles injections, for lip augmentation and contouring other body parts. Cosmetic products predominantly use decomposition fragments of HA of relatively low molecular weights (e.g. 50 to 130 kD).

An object of the present invention is to improve the efficacy of hyaluronic acid in tissues near bones, and possibly in bones themselves by an appropriate supply of hyaluronic acid.

Accordingly, the present invention refers to the use of a gel containing hyaluronic acid for the healing and/or regeneration of bones and bone-surrounding tissues in a human or a vertebrate by injecting the gel containing hyaluronic acid in a cross-linked form or as a mixture of cross-linked and non-crosslinked forms into the periosteum of bone.

Figure 1:
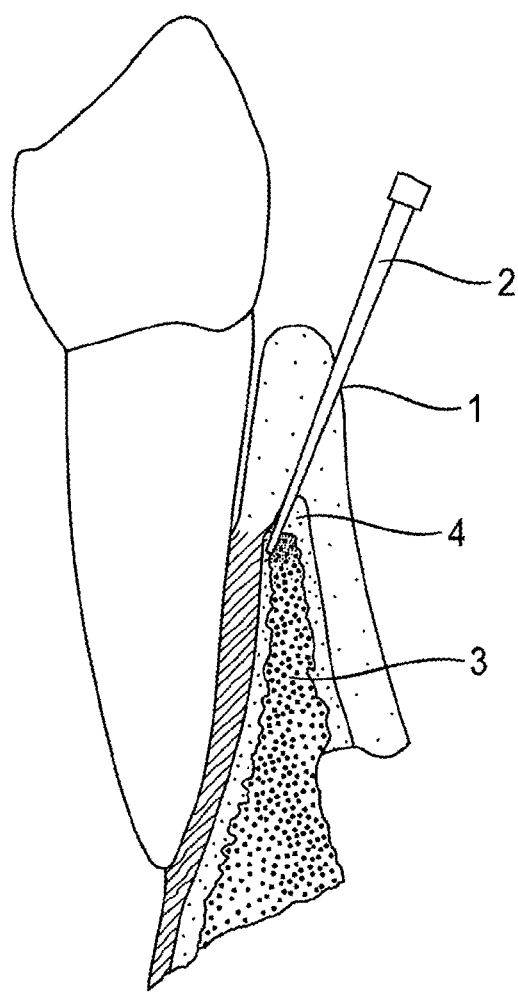
FIG. 1 is a schematic view showing the injection of hyaluronic acid into the periosteum of alveolar bone.

The hyaluronic acid used in the present invention may be present in a cross-linked form or as a mixture of non-crosslinked and cross-linked forms.

The non-crosslinked form, which is preferably used herein, has a molecular weight range of about 730 kD to about 1,500 kD.

A great number of cross-linked forms of HA are commercially available. They are usually injected as aqueous solutions in gel form. Basically, a distinction is made between particulate cross-linked HA with particle sizes in a range of only a few µm to about 1000 µm, and homogenous, non-particulate, cross-linked monophasic HA, although in practice, these differences may not be as important as commonly assumed.

A great number of cross-linked HA products have been developed, predominantly for use as dermal fillers. In this respect, chain lengths and cross-linkers may vary widely.

There are cross-linked HAs with a monomodal chain length distribution and those with a bimodal chain length distribution (relatively short chains and long chains), the latter being able to form an interpenetrating network after cross-linking. Their chain length is generally 1,000 to 3,000 kD, but may also be shorter or longer.

Common cross-linkers are e.g. glutaraldehyde, 1-ethyl-3-(3-dimethylaminopropyl) carbodiimide (EDC), poly(ethylene glycol) diglycidylether (EX 801), divinyl sulfone (DVS), 1,4-butanediol diglycidylether (BDDE), and 1,2,7,8-diepoxyoctane.

Cross-linked HA is used in gel form in an aqueous medium. In commercially available products, the concentration of cross-linked HA in aqueous media generally varies from about 18 to about 26 mg cross-linked HA/ml aqueous medium, e.g. phosphate buffer. As an alternative, the ratio (w./vol.) of hyaluronic acid to aqueous medium, e.g. phosphate buffer, may be in a range of 1:35 to 1:45.

The gel used according to the present invention may contain other drugs or excipients, such as preservatives, or other common pharmaceutical excipients.

Some common cross-linked HA products which are commercially available for use as dermal fillers are e.g. Restylane® (Fa. Galderma), Juvederm® (Fa. Allergan), Belotero® (Fa. Merz), Hyal® (Fa. Merz). Stylage® (Fa. Laboraitres Vivacy), Puragen® (Fa. Menotr Corporation), Emervel® (Fa. Galderma), and Teosyal® (Fa. Laboratoires Teoxane).

Periosyal® (Fa. Laboratoires Teoxane) is used especially in dentistry.

Surprisingly, it has now been found that the injection of the above-described HA preparations or similar preparations into the periosteum of bone leads to an unexpectedly good healing and/or regeneration of bones and tissue surrounding the bones which had been affected by inflammation, for example.

The periosteum is a highly vascular connective tissue, which surrounds all bones except at the joints and muscle attachment sites. Its thickness is generally about 0.070 to 0.150 mm. It comprises at least two layers, an inner cambium or osteogenic layer and an outer fiber layer. The inner layer contains a large number of osteoblasts and osteogenic precursor cells, the outer layer consists of densely packed collagen fibers, fibroblasts and their precursor cells.

For injections into the periosteum, a monophasic gel preparation with cross-linked HA or a gel preparation of cross-linked HA having very small particles in a range of not more than 20 µm, which may also contain non crosslinked HA, is preferred. For example, it is advantageous to inject an amount of 0.01 to 0.03 ml HA preparation per injection. A preferred product is e.g. HA of shorter chain length, cross-linked with 5.0 to 10.0 percent by weight of 1,4-butanediol diglycidylether (BDDE), at a concentration of 25 mg HA in phosphate buffer, pH 7.3, ad 1 ml (commercially available as Periosyal® Fill from Laboratoires Teoxane), or HA of long chain length, cross-linked with 1.9 to 4.0 percent by weight of 1,4-butanediol diglycidylether (BDDE), at a concentration of 25 mg HA in phosphate buffer, pH 7.3, ad 1 ml (commercially available as Periosyal® Shape from Laboratoires Teoxane).

The injection of the HA preparation into the periosteum is accomplished using a thin pointed needle, preferably with an outer diameter of 0.30-0.50 mm (EN ISO 9626), or by an electronic pen needle of similar diameter. In practice, the needle will be slowly inserted towards the bone, until the compact bone offers a resistance, which cannot be overcome. The preparation is then slowly pushed through the needle and into the periosteum, e.g. in the course of 10 s to 2 min, preferably 20 s to 60 s. Only part of the injected HA preparation may remain in the periosteum, and excessive preparation may flow over into the surrounding structures.

This technique will be described in more detail in the following example with reference to an injection into the periosteum of an alveolar bone.

In addition to the injection into the periosteum, the same or a different HA preparation can also be injected into soft tissue surrounding the bone's periosteum. This will also be described in more detail in the following example using an injection into the periodontal ligament of teeth.

The effect of the injection into the periosteum is the healing of an inflammation in soft tissue surrounding the bone and in the inflamed bone itself, as well as the regeneration of these structures, which will also be described in more detail using an example from the dental field. If necessary, the injection can be repeated once or twice with intervals of 1 to 2 weeks, for example.

Possible side effects of the injection include swelling, redness, pain, itching and sensitivity at the injection site.

EXAMPLE

Figure 2:
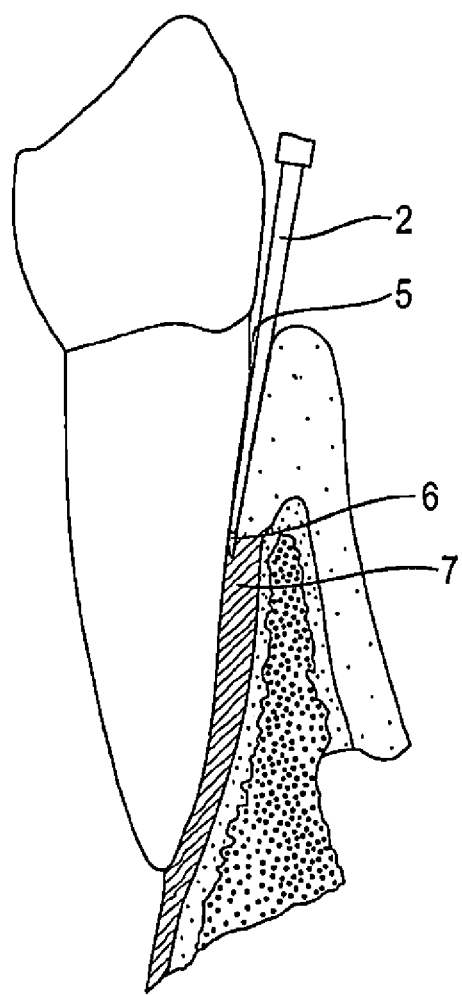
FIG. 2 is a schematic view showing the injection of hyaluronic acid into the periodontal ligament.

The periosteum of 10 patients with periodontitis, whose interdental papilla was swollen and inflamed, with deep pockets of a depth of 3 and more frequently of 7 to 9 mm (FIG. 1), and whose alveolar bones had already been affected, i.e. were decreased, as could be seen from an x-ray image, were slowly injected through the periodontal ligament in a distance of about 3 to 4 mm from the tip of the papilla (1 in FIG. 1) with 0.02 to 0.03 ml Periosyal® Fill (Laboratoires Texane) in the course of 20-40 s, with a syringe needle 2 (FIG. 2) having an outer diameter of 0.30 mm (according to EN ISO 9626) by introducing the syringe needle at an angle of about 20° with respect to the tooth up to a point where the compact bone resisted a further insertion of the needle.

In addition to that, the same amount of Periosyal® Fill (Laboratoires Texane) was injected by inserting the syringe needle 2 (FIG. 2) into the left and right sulcus gingivae 5 (FIG. 2) until it reached the bottom 6 (FIG. 2) of the sulcus gingivae, and then further by gently pushing the needle into the periodontal ligament 7 (FIG. 2) and slowly injecting the gel in the course of 20-60 s, until it started to escape from the periodontal ligament 7 and the sulcus gingivae 5.

After healing, the initially deep pockets of the sulcus gingivae were reduced to only a few mm (e.g. From 7-9 mm to 1-2 mm), the diastema was largely closed, bleeding as a result of pocket measurement or probing was reduced, and the tissue appeared tightened, and in addition to that, x-ray images showed a significant regeneration of the alveolar bone which had been affected by inflammation.

The physiological mechanism underlying the surprisingly good healing and regeneration of the periodontal ligament and the alveolar bone is not fully understood. The bacteriostatic effect of hyaluronic acid certainly plays a major role, but there appear to be other factors, too, for a treatment of the periodontal ligament alone, without an injection into the periosteum of the alveolar bone, does not bring about such a treatment success or at least to a much lesser extent.

It should be noted that a conventional periodontal treatment would result in a recessed papilla and black corners (i.e. corners without gums) appearing between teeth. A regeneration of bone would not be expected, either.

The invention claimed is:

1. A method of treating and/or regenerating a bone and bone-surrounding tissue of a human or a vertebrate in need thereof, wherein the method comprises injecting into a periosteum of an alveolar bone a gel which comprises hyaluronic acid in cross-linked form or as a mixture of cross-linked and non-crosslinked forms.

2. The method of claim 1, wherein hyaluronic acid in non-crosslinked form comprises a hyaluronic acid of non-animal origin having a molecular weight of about 730 kD to about 1,500 kD.

3. The method of claim 1, wherein hyaluronic acid in cross-linked form comprises a non-animal hyaluronic acid cross-linked with 5 to 10% by weight of butanediol diglycidylether.

4. The method of claim 1, wherein hyaluronic acid in cross-linked form comprises a non-animal hyaluronic acid cross-linked with 1.9 to 4% by weight of butanediol diglycidylether.

5. The method of claim 1, wherein the hyaluronic acid is present in the gel in a phosphate buffer having a pH of 7.3.

6. The method of claim 5, wherein a ratio (w./vol.) of hyaluronic acid to phosphate buffer is in a range of from 1:35 to 1:45.

7. The method of claim 1, wherein the hyaluronic acid gel is injected in an amount of from 0.01 to 0.03 ml using a syringe needle or a needle with an outer diameter of 0.30-0.50 mm (EN ISO 9626) or an electronic pen needle having an outer diameter of 0.30-0.50 mm.

8. The method of claim 1, wherein the hyaluronic acid gel is injected into the periosteum over a period of from 10 s to 2 min.

9. The method of claim 1, wherein the method further comprises injecting the same or a different hyaluronic acid gel into a periodontal ligament.

10. The method of claim 1, wherein the treated bone is a bone of a human.

11. The method of claim 1, wherein the treated bone is a bone of a vertebrate.

12. A method of treating and/or regenerating a bone and bone-surrounding tissue of a human or a vertebrate in need thereof, wherein the method comprises injecting into a periosteum of the bone a gel which comprises hyaluronic acid in cross-linked form or as a mixture of cross-linked and non-crosslinked forms and wherein the method further comprises injecting the same or a different hyaluronic acid gel into a periodontal ligament.

13. The method of claim 12, wherein hyaluronic acid in non-crosslinked form comprises a hyaluronic acid of non-animal origin having a molecular weight of about 730 kD to about 1,500 kD.

14. The method of claim 12, wherein hyaluronic acid in cross-linked form comprises a non-animal hyaluronic acid cross-linked with 5 to 10% by weight of butanediol diglycidylether.

15. The method of claim 12, wherein hyaluronic acid in cross-linked form comprises a non-animal hyaluronic acid cross-linked with 1.9 to 4% by weight of butanediol diglycidylether.

16. The method of claim 12, wherein the hyaluronic acid is present in the gel in a phosphate buffer having a pH of 7.3.

17. The method of claim 16, wherein a ratio (w./vol.) of hyaluronic acid to phosphate buffer is in a range of from 1:35 to 1:45.

18. The method of claim 12, wherein the hyaluronic acid gel is injected into the periosteum over a period of from 10 s to 2 min.

19. A method of treating and/or regenerating a bone and bone-surrounding tissue of a human or a vertebrate in need thereof, wherein the method comprises injecting into a periosteum of the bone a gel which comprises hyaluronic acid in cross-linked form or as a mixture of cross-linked and non-crosslinked forms and wherein the hyaluronic acid gel is injected in an amount of from 0.01 to 0.03 ml using a syringe needle or a needle with an outer diameter of 0.30-0.50 mm (EN ISO 9626) or an electronic pen needle having an outer diameter of 0.30-0.50 mm.

20. The method of claim 19, wherein the method further comprises injecting the same or a different hyaluronic acid gel into a periodontal ligament.

\* \* \* \* \*